(12) United States Patent
Zehavi et al.

(10) Patent No.: US 12,268,457 B2
(45) Date of Patent: Apr. 8, 2025

(54) VERSATILE MULTI-ARM ROBOTIC SURGICAL SYSTEM

(71) Applicant: MAZOR ROBOTICS LTD., Caesarea (IL)

(72) Inventors: Eliyahu Zehavi, Haifa (IL); Moshe Shoham, Hoshaya (IL); Yonatan Ushpizin, Kibbutz Glil Yam (IL)

(73) Assignee: MAZOR ROBOTICS LTD., Caesarea (IL)

( * ) Notice: Subject to any disclaimer, the term of this patent is extended or adjusted under 35 U.S.C. 154(b) by 424 days.

(21) Appl. No.: 17/285,374

(22) PCT Filed: Oct. 15, 2019

(86) PCT No.: PCT/IB2019/058795
§ 371 (c)(1),
(2) Date: Apr. 15, 2021

(87) PCT Pub. No.: WO2020/079596
PCT Pub. Date: Apr. 23, 2020

(65) Prior Publication Data
US 2021/0338348 A1    Nov. 4, 2021

Related U.S. Application Data

(60) Provisional application No. 62/745,497, filed on Oct. 15, 2018.

(51) Int. Cl.
*A61B 34/30* (2016.01)
*A61B 6/00* (2006.01)
(Continued)

(52) U.S. Cl.
CPC ............ *A61B 34/30* (2016.02); *A61B 6/4458* (2013.01); *A61B 8/4218* (2013.01); *A61B 34/20* (2016.02);
(Continued)

(58) Field of Classification Search
None
See application file for complete search history.

(56) References Cited

U.S. PATENT DOCUMENTS

| 5,329,933 A | 7/1994 | Graf |
| 6,152,890 A | 11/2000 | Kupfer et al. |

(Continued)

FOREIGN PATENT DOCUMENTS

| CA | 2958013 | 4/2017 |
| CN | 108186120 | 6/2018 |

(Continued)

OTHER PUBLICATIONS

Invitation to Pay Additional Fees for International (PCT) Patent Application No. PCT/IL2022/050603, dated Oct. 6, 2022, 13 pages.
(Continued)

*Primary Examiner* — Peter D Nolan
*Assistant Examiner* — Jacob Kent Besteman-Street
(74) *Attorney, Agent, or Firm* — Sheridan Ross P.C.

(57) ABSTRACT

A robotic surgical system comprising at least two robotic arms having co-ordinate systems known relative to each other, one of the arms carrying an X-ray source, and the other an imaging detector plate. The arms are disposed to enable an image to be generated on the region of interest of a subject. One of the arms can additionally or alternatively carry a surgical tool or tool holder, such that the pose of the tool is known in the same co-ordinate system as that of an image generated by the X-ray source and detector. Consequently, any surgical procedure planned on such an X-ray image can be executed by the tool with high accuracy, since the tool position is known in the image frame of reference. This enables the surgeon to accurately position his tool in a real-time image without the need for an external registration procedure.

20 Claims, 4 Drawing Sheets

(51) Int. Cl.
*A61B 8/00* (2006.01)
*A61B 34/20* (2016.01)
*B25J 9/16* (2006.01)
*B25J 13/08* (2006.01)
*G01T 1/161* (2006.01)
*G06T 7/30* (2017.01)

(52) U.S. Cl.
CPC ............ *B25J 9/1697* (2013.01); *B25J 13/08* (2013.01); *G01T 1/161* (2013.01); *G06T 7/30* (2017.01); *A61B 2034/2063* (2016.02); *G06T 2207/10116* (2013.01); *G06T 2207/10132* (2013.01); *G06T 2207/30004* (2013.01); *G06T 2207/30241* (2013.01)

(56) References Cited

U.S. PATENT DOCUMENTS

| | | |
|---|---|---|
| 6,200,024 B1 * | 3/2001 | Negrelli ............... A61B 6/4476 378/197 |
| 6,435,715 B1 | 8/2002 | Betz et al. |
| 6,582,121 B2 | 6/2003 | Crain et al. |
| 6,644,852 B2 | 11/2003 | Crain et al. |
| 7,198,630 B2 | 4/2007 | Lipow |
| 7,567,834 B2 | 7/2009 | Clayton et al. |
| 7,708,741 B1 | 5/2010 | Bonutti |
| 7,899,226 B2 | 3/2011 | Pescatore et al. |
| 7,907,166 B2 | 3/2011 | Lamprecht et al. |
| 8,073,528 B2 | 12/2011 | Zhao et al. |
| 8,108,072 B2 | 1/2012 | Zhao et al. |
| 8,147,503 B2 | 4/2012 | Zhao et al. |
| 8,392,022 B2 | 3/2013 | Ortmaier et al. |
| 8,568,317 B1 | 10/2013 | Gharib et al. |
| 8,611,495 B2 | 12/2013 | Maschke |
| 8,721,566 B2 | 5/2014 | Connor et al. |
| 8,781,630 B2 | 7/2014 | Banks et al. |
| 8,870,889 B2 | 10/2014 | Frey |
| 9,050,728 B2 | 6/2015 | Ban et al. |
| 9,259,276 B2 | 2/2016 | Mintz et al. |
| 9,259,278 B2 | 2/2016 | Jensen |
| 9,259,282 B2 | 2/2016 | Azizian et al. |
| 9,307,894 B2 | 4/2016 | von Grunberg et al. |
| 9,402,689 B2 | 8/2016 | Prisco et al. |
| 9,592,096 B2 | 3/2017 | Maillet et al. |
| 9,649,072 B2 | 5/2017 | Ragnarsdottir et al. |
| 9,662,174 B2 | 5/2017 | Taylor et al. |
| 9,687,301 B2 | 6/2017 | Lee et al. |
| 9,767,608 B2 | 9/2017 | Lee et al. |
| 9,789,313 B2 | 10/2017 | Lipani |
| 9,888,966 B2 | 2/2018 | Farritor et al. |
| 9,895,813 B2 | 2/2018 | Blumenkranz et al. |
| 9,969,090 B2 | 5/2018 | Warashina et al. |
| 10,076,385 B2 | 9/2018 | Shoham et al. |
| 10,149,729 B2 | 12/2018 | Smaby et al. |
| 10,271,832 B2 | 4/2019 | O'Neil et al. |
| 10,299,880 B2 | 5/2019 | Ramirez Luna et al. |
| 10,368,054 B2 | 7/2019 | Panescu et al. |
| 10,383,765 B2 | 8/2019 | Alvarez et al. |
| 10,390,895 B2 | 8/2019 | Henderson et al. |
| 10,456,076 B2 | 10/2019 | Liu |
| 10,456,211 B2 | 10/2019 | McAfee |
| 10,512,413 B2 | 12/2019 | Schepis et al. |
| 10,561,384 B2 | 2/2020 | Tanaka et al. |
| 10,668,625 B2 | 6/2020 | Kuroda et al. |
| 10,675,098 B2 | 6/2020 | Zhao et al. |
| 10,675,107 B2 | 6/2020 | Steger et al. |
| 10,812,778 B1 | 10/2020 | Wang et al. |
| 11,298,195 B2 | 4/2022 | Ye et al. |
| 2004/0122427 A1 | 6/2004 | Holmes |
| 2005/0096502 A1 | 5/2005 | Khalili |
| 2006/0241414 A1 | 10/2006 | Nowlin et al. |
| 2006/0258938 A1 | 11/2006 | Hoffman et al. |
| 2007/0106307 A1 | 5/2007 | Bodduluri et al. |
| 2007/0232958 A1 | 10/2007 | Donofrio et al. |
| 2009/0088634 A1 * | 4/2009 | Zhao ................... A61B 1/00193 600/425 |
| 2011/0069818 A1 | 3/2011 | Muller |
| 2011/0087238 A1 | 4/2011 | Wang et al. |
| 2011/0106102 A1 * | 5/2011 | Balicki ............... A61B 3/1005 606/1 |
| 2011/0172566 A1 | 7/2011 | Kawchuk |
| 2011/0172720 A1 | 7/2011 | Metcalf, Jr. et al. |
| 2011/0276179 A1 * | 11/2011 | Banks .................. A61B 34/76 700/264 |
| 2012/0029694 A1 | 2/2012 | Mueller |
| 2012/0041562 A1 | 2/2012 | Shachar et al. |
| 2013/0012831 A1 | 1/2013 | Schmitz et al. |
| 2013/0096574 A1 | 4/2013 | Kang et al. |
| 2013/0211419 A1 * | 8/2013 | Jensen ................. A61B 6/4441 606/130 |
| 2013/0268007 A1 | 10/2013 | Rezach et al. |
| 2014/0163736 A1 | 6/2014 | Azizian et al. |
| 2014/0179997 A1 | 6/2014 | von Grunberg et al. |
| 2014/0188132 A1 * | 7/2014 | Kang ................... A61B 6/4441 606/130 |
| 2014/0253684 A1 | 9/2014 | Kumar et al. |
| 2014/0309659 A1 | 10/2014 | Roh et al. |
| 2014/0350571 A1 * | 11/2014 | Maillet ................. A61B 34/30 901/8 |
| 2015/0297177 A1 | 10/2015 | Boctor et al. |
| 2016/0081754 A1 | 3/2016 | Kostrzewski et al. |
| 2016/0184032 A1 | 6/2016 | Romo et al. |
| 2017/0273614 A1 | 9/2017 | Giphart et al. |
| 2018/0064497 A1 | 3/2018 | Hussain et al. |
| 2018/0193101 A1 | 7/2018 | Hashimoto |
| 2018/0263530 A1 | 9/2018 | Jung |
| 2018/0307314 A1 | 10/2018 | Connor |
| 2018/0333061 A1 | 11/2018 | Pracyk et al. |
| 2018/0368931 A1 | 12/2018 | Hongo et al. |
| 2019/0069957 A1 | 3/2019 | Barral et al. |
| 2019/0125460 A1 | 5/2019 | Maillet et al. |
| 2019/0206565 A1 | 7/2019 | Shelton, IV |
| 2019/0307519 A1 | 10/2019 | Popovic |
| 2019/0357884 A1 | 11/2019 | Williams et al. |
| 2019/0374299 A1 | 12/2019 | Peine |
| 2020/0015806 A1 | 1/2020 | Scheib et al. |
| 2020/0015923 A1 | 1/2020 | Scheib et al. |
| 2020/0054215 A1 | 2/2020 | Roche |
| 2020/0060775 A1 | 2/2020 | Bonutti |
| 2020/0069377 A1 | 3/2020 | Finley et al. |
| 2020/0113637 A1 | 4/2020 | Ida et al. |
| 2020/0169673 A1 | 5/2020 | King et al. |
| 2020/0179065 A1 | 6/2020 | Crawford et al. |
| 2020/0205900 A1 | 7/2020 | Buckland et al. |
| 2020/0261160 A1 | 8/2020 | Peine et al. |
| 2020/0261297 A1 | 8/2020 | Strydom et al. |
| 2020/0360099 A1 | 11/2020 | Smaby et al. |
| 2020/0405403 A1 | 12/2020 | Shelton, IV et al. |
| 2021/0029307 A1 | 1/2021 | King et al. |
| 2021/0298590 A1 | 9/2021 | Ayvali et al. |
| 2021/0402603 A1 | 12/2021 | Murphy et al. |
| 2022/0096188 A1 | 3/2022 | Ellman et al. |
| 2022/0160445 A1 | 5/2022 | Meglan et al. |
| 2022/0241026 A1 | 8/2022 | Shoham et al. |
| 2022/0241032 A1 | 8/2022 | Zucker et al. |
| 2022/0395342 A1 | 12/2022 | Weiss et al. |

FOREIGN PATENT DOCUMENTS

| | | |
|---|---|---|
| CN | 109171745 | 1/2019 |
| DE | 10042599 | 3/2002 |
| DE | 102012004506 | 9/2013 |
| DE | 102015217059 | 3/2017 |
| EP | 2289452 | 3/2011 |
| EP | 2757948 | 7/2014 |
| EP | 2467074 | 1/2019 |
| EP | 3492046 | 6/2019 |
| EP | 3492047 | 6/2019 |
| EP | 2739231 | 9/2019 |
| EP | 3551983 | 10/2019 |
| EP | 3060157 | 12/2019 |
| EP | 3609422 | 2/2020 |

(56) References Cited

FOREIGN PATENT DOCUMENTS

| | | |
|---|---|---|
| EP | 2879608 | 3/2020 |
| GB | 2156983 | 10/1985 |
| JP | 5207490 | 6/2013 |
| JP | 2017-512299 | 5/2017 |
| JP | 2019-524230 | 9/2019 |
| KR | 10-2019-114052 | 10/2019 |
| RO | 132416 | 3/2018 |
| WO | WO 95/01757 | 1/1995 |
| WO | WO 96/29930 | 10/1996 |
| WO | WO 00/35366 | 6/2000 |
| WO | WO 2007/025218 | 3/2007 |
| WO | WO 2007/038510 | 4/2007 |
| WO | WO 2010/068005 | 6/2010 |
| WO | WO 2011/149845 | 12/2011 |
| WO | WO 2012/168534 | 12/2012 |
| WO | WO 2014/106262 | 7/2014 |
| WO | WO 2017/002143 | 1/2017 |
| WO | WO 2018/203903 | 11/2018 |
| WO | WO 2019/036006 | 2/2019 |
| WO | WO 2019/206340 | 10/2019 |
| WO | WO 2020/072255 | 4/2020 |
| WO | WO 2020/079596 | 4/2020 |
| WO | WO 2020/118244 | 6/2020 |
| WO | WO 2020/201353 | 10/2020 |

OTHER PUBLICATIONS

International Search Report and Written Opinion for International (PCT) Patent Application No. PCT/IL2022/050603, dated Nov. 28, 2022, 21 pages.

International Preliminary Report on Patentability for International (PCT) Patent Application No. PCT/IB2021/058420, dated Apr. 13, 2023 10 pages.

Official Action with English Translation for Japan Patent Application No. 2021-514567, dated May 11, 2023, 12 pages.

"Robotic Assisted Systems," Intuitive Surgical, Jul. 2019, 5 pages.

Abdelaal et al. "A multi-camera, multi-view system for training and skill assessment for robot-assisted surgery," International Journal of Computer Assisted Radiology and Surgery, May 2020, vol. 15, pp. 1369-1377.

Boctor et al. "A Dual-Armed Robotic System for Intraoperative Ultrasound Guided Hepatic Ablative Therapy: A Prospective Study," IEEE, Proceedings of the 2004 IEEE International Conference on Robotics & Automation, New Orleans, LA, Apr. 2004, pp. 2517-2522.

Joskowicz "Computer-aided surgery meets predictive, preventive, and personalized medicine," EPMA Journal, 2017, vol. 8, 4 pages.

Khandalavala "Emerging surgical robotic technology: a progression toward microbots," Annals of Laparoscopic and Endoscopic Surgery, Jan. 2020, vol. 5, Article 3, 18 pages.

Kim et al. "Robot-Assisted Cardiac Surgery Using the Da Vinci Surgical System: A Single Center Experience," Korean Journal of Thoracic and Cardiovascular Surgery, 2015, vol. 48, pp. 99-104.

Kumar et al. "Emerging role of robotics in urology, Journal of Minimal Access Surgery," Oct. 2005, vol. 1, No. 4, pp. 202-210.

Li et al. "Design of a Multi-Arm Surgical Robotic System for Dexterous Manipulation," Journal of Mechanisms and Robotics, Dec. 2016, vol. 8, article 061017, 10 pages.

Staub "Micro Endoscope based Fine Manipulation in Robotic Surgery," Technische Universitat Munchen Lehrstuhl Robotic und Echtzeitsysteme, Dissertation, Apr. 2013, 146 pages.

Invitation to Pay Additional Fees for International (PCT) Patent Application No. PCT/IL2022/050126, dated May 27, 2022, 11 pages.

International Search Report and Written Opinion for International (PCT) Patent Application No. PCT/IL2022/050126, dated Jul. 18, 2022, 18 pages.

Extended Search Report for European Patent Application No. 19872498.1, dated Jun. 9, 2022, 9 pages.

International Search Report and Written Opinion prepared by the Israel Patent Office on Dec. 31, 2019, for International Application No. PCT/IB2019/058795.

International Search Report and Written Opinion for International (PCT) Patent Application No. PCT/IB2021/058420, dated Nov. 29, 2021 16 pages.

"Robot-Assisted Laparoscopic Procedures," EBESCO Information Services, Updated May 2014, 6 pages [retrieved online from: www.wkhs.com/cancer/cancer-treatment-services/surgery/robotic-surgery/robot-assisted-laparoscopic-procedures].

Cao et al. "A Novel Robotic Suturing System for Flexible Endoscopic Surgery," IEEE, 2019 International Conference on Robotics and Automation (ICRA), May 20-24, 2019, Montreal, Canada, 7 pages.

He et al. "A Multi-Function Force Sensing Instrument for Variable Admittance Robot Control in Retinal Microsurgery," 2014 IEEE International Conference on Robotics and Automation (ICRA), 2014, pp. 1411-1418.

Kong et al. "Da Vinci Tool Torque Mapping over 50,000 Grasps and its Implications on Grip Force Estimation Accuracy," 2018 International Symposium on Medical Robotics (ISMR), 2018, 6 pages.

Matthews "How better data, 5G, and surgical robots will improve healthcare," The Robot Report, Sep. 29, 2019, 12 pages [retrieved online from: www.therobotreport.com/better-data-advancing-healthcare-robotics].

Seibold "An Advanced Force Feedback Tool Design for Minimally Invasive Robotic Surgery," Technische Universität München, May 15, 2012, Doctoral Engineers dissertation, 218 pages.

Tian et al. "A Robot-Assisted Surgical System Using a Force-Image Control Method for Pedicle Screw Insertion," PLOS One, Jan. 2014, vol. 9, No. 1, article e86346, 9 pages.

Valeo "Scarless Surgery: The benefits and drawbacks of robotic thryroidectomy," ENTtoday, Apr. 1, 2010, 4 pages [retrieved online from: www.enttoday.org/article/scarless-surgery-the-benefits-and-drawbacks-of-robotic-thryroidectomy/].

Vivek et al. "Study of Neuroarm and Force Sensing Grippers in Robo-Assisted Neurosurgery," International Journal of Current Engineering and Technology, Mar. 2016, Special Issue 4, pp. 444-447.

Official Action with English Translation for Japan Patent Application No. 2021-514567, dated Sep. 26, 2023, 12 pages.

Official Action for U.S. Appl. No. 17/344,658, dated Aug. 4, 2023 6 pages Restriction Requirement.

Official Action for U.S. Appl. No. 17/344,658, dated Oct. 25, 2023 9 pages.

Official Action for U.S. Appl. No. 17/575,404, dated Jun. 21, 2024 13 pages.

Official Action for U.S. Appl. No. 17/344,658, dated Jul. 15, 2024 10 pages.

Aranda-Valera et al. "Measuring Spinal Mobility Using an Inertial Measurement Unit System: A Validation Study in Axial Spondyloarthritis," Diagnostics, 2020, vol. 10, No. 6, Article 426, 13 pages.

Dai et al. "Vibration-Based Milling Condition Monitoring in Robot-Assisted Spine Surgery," IEEE/AMSE Transactions on Mechatronics, Dec. 2015, vol. 20, No. 6, pp. 3028-3039.

Haratian et al. "Toward Flexibility in Sensor Placement for Motion Capture Systems: A Signal Processing Approach," IEEE Sensors Journal, Mar. 2014, vol. 14, No. 3, pp. 701-709.

Hennersperger et al. "Towards MRI-Based Autonomous Robotic US Acquisitions: A First Feasibility Study," IEEE Transactions on Medical Imaging, Feb. 2017, vol. 36, No. 2, pp. 538-548.

Leroy "Analysis of the spine through a multibody model and IMU technology," Ecole polytechnique de Louvain, Université catholique de Louvain, 2019, 90 pages [retrieved online Oct. 29, 2020 from: hdl.handle.net/2078.1/thesis:19491].

Stolka et al. "Improving Navication Precision of Milling Operations in Surgical Robotics," Proceedings of the 2006 IEEE/RSJ International Conference on Intelligent Robotics and Systems, Oct. 9-15, 2008, Beijing, China, pp. 2351-2357.

Vandini et al. "Unified Tracking and Shape Estimation for Concentric Tube Robots," IEEE Transactions on Robotics, Aug. 2017, vol. 33, No. 4, pp. 901-915.

(56) References Cited

OTHER PUBLICATIONS

Voinea et al. "Measurement and Geometric Modelling of Human Spine Posture for Medical Rehabilitation Purposes Using a Wearable Monitoring System Based on Inertial Sensors," Sensors, 2017, vol. 17, No. 1, Article 3, 19 pages.
International Search Report and Written Opinion for International (PCT) Patent Application No. PCT/IL2022/050141, dated Jun. 8, 2022, 16 pages.
Official Action for U.S. Appl. No. 17/464,300, dated Aug. 20, 2024 31 pages.
Official Action for U.S. Appl. No. 17/583,788, dated Aug. 19, 2024 6 pages Restriction Requirement.
Official Action with Machine Translation for China Patent Application No. 201980067844.9, dated Mar. 1, 2024, 27 pages.
Official Action for U.S. Appl. No. 17/344,658, dated Mar. 21, 2024 12 pages.
Li et al. "Robotic Systems for MIR-Guided Stereotactic Neurosurgery," IEEE Transactions on Biomedical Engineering, Apr. 2015, vol. 62, No. 4, pp. 1077-1088.
Notice of Allowance for U.S. Appl. No. 17/464,300, dated Nov. 20, 2024 10 pages.
Official Action for U.S. Appl. No. 17/575,404, dated Oct. 25, 2024 20 pages.
Official Action for U.S. Appl. No. 17/344,658, dated Dec. 16, 2024 15 pages.
Official Action with English Translation for Japan Patent Application No. 2024-009920, dated Jan. 15, 2025, 6 pages.

\* cited by examiner

VERSATILE MULTI-ARM ROBOTIC SURGICAL SYSTEM

CROSS REFERENCE TO RELATED APPLICATIONS

This application is a national stage application under 35 U.S.C. 371 and claims the benefit of PCT Application No. PCT/IB2019/058795 having an international filing date of 15 Oct. 2019, which designated the United States, which PCT application claimed the benefit of U.S. Provisional Patent Application No. 62/745,497 filed 15 Oct. 2018, the entire disclosures of each of which are incorporated herein by reference.

FIELD OF THE INVENTION

The present invention relates to the field of robotic surgery, especially systems involving the coordination of imaging of the patient with robotic surgical procedures.

BACKGROUND

There exist a number of surgical robotic systems, which enable accurate positioning or operation of surgical tools in the performance of surgical procedures. One of the primary problems in such systems is the ability to relate the position and orientation, i.e. the pose, of the surgical tools, with the preoperative surgical plan, or with intraoperative images taken during the surgery. Relating the pose of surgical tools with a preoperative surgical plan is a problem which is solved by using a registration procedure, usually between the features on which it is desired to operate according to the surgical plan, as shown in the preoperative images, and the real-life intraoperative position of the robotically guided tools, and the patient on the operating bed. The preoperative images are usually three dimensional images, such as CT or MRI image sets, while the intraoperative surgical situation is generally obtained by use of fluoroscopic images obtained using a C-arm imaging system.

There further exist a number of systems in which the historically conventional C-arm system, having a rigid support member circumscribing the patient, with an X-ray source on one end of the member and an X-ray collector or detector plate on the other end of the member, has been superseded by "virtual C-arms" having robotically aligned elements. In such systems, an X-ray source and a detector element are carried on the ends of separate robotically activated arms, such that they can be positioned at opposite sides of the patient. The exact pose of the X-ray fluoroscopic image can be selected by means of robotic control of the arms respectively carrying the source and the imaging element. Such systems have been described in U.S. Pat. No. 6,582,121 for "X-Ray Positioner with Side-Mounted Independently Articulated Arms" to M. Crain et al, assigned to GE Medical Systems Global Technology, and in U.S. Pat. No. 6,644,852 for "Automatically Reconfigurable X-Ray Positioner" also to M. Crain and also assigned to GE Medical Systems. In U.S. Pat. No. 8,611,495 for "Biplane X-Ray Imaging System" to M. Maschke, assigned to Siemens AG, there is described an imaging system having two recording units disposed on C-arms in different planes. This patent also mentions the possibility of having each X-ray tube assembly and X-ray detector disposed individually on retaining elements such as robotic arms. Similar systems using X-ray source and X-ray detector panel mounted on separate robotic arms are also shown in U.S. Pat. No. 6,200,024 for "Virtual C-Arm Robotic Positioning System for Use in Radiographic Imaging Equipment" to D. Negrelli, assigned to Picker International. Patent application No. DE 10 2015 217059 A1 by M. Hörning, filed by Siemens Healthcare GmbH, also describes an X-ray system having the X-ray emitter and X-ray receiver on separately controlled support arms. US published patent application No. 2011/0069818 to M. Muller, assigned to Kuka Roboter GmbH, also describes an X-ray system with the source and receiver on separate robotic arms. U.S. Pat. No. 6,435,715 to R. Betz et al, for "Radiography Device" assigned to Siemens AG, also describes a system having an X-ray source and an X-ray receiver mounted on different robotic arms, to generate a virtual C-arm arrangement. The robotic control ensures that the X-ray source is always oriented opposite to the X-ray receiver for the purpose of acquiring images. The patient position may be related to the robotic co-ordinate system by means of image analysis of markers using an external camera system connected to the robotic control system.

U.S. Pat. No. 8,781,630 for "Imaging Platform to Provide Integrated Navigation Capabilities for Surgical Guidance" to S. A. Banks et al, assigned to the University of Florida Research Foundation Inc., describes a system which includes two robotic arm systems, one holding an imaging source, and the other holding an imaging sensor, like the systems previously mentioned above. A third robotic arm system can be included as a surgeon guided tool-holder. The tool is manually guided by the surgeon using haptic control and optional force feedback. The spatial poses of the imaging source robotic arm, and the tool-holder robotic arm can be related to each other by using X-ray calibration targets on the imaging source arm and on the tool-holding arm, or a tracking system, using an electromagnetic or optical tracker which can locate a localizing marker on the imaging source arm and on the tool-holding arm. The tool tip can be registered with the navigation reference frames using a touch device.

However, the above described systems are limited mostly to imaging functionality, or to haptic systems, in which the systems mimic robotically controlled conventional C-arm imaging functionality The disclosures of each of the publications mentioned in this section and in other sections of the specification, are hereby incorporated by reference, each in its entirety.

SUMMARY

There exists a need for a more comprehensive robotically controlled virtual C-arm system that overcomes at least some of the disadvantages of prior art systems and methods. Modern robotic-guided surgery requires the ability to automatically relate any imaging function, to the current execution of the surgical plan. The present disclosure describes new exemplary systems for executing robotically guided surgery, in combination with an imaging system that enables a robotically guided tool to be related to the image or images generated with the imaging system. The system is based on a robotically controlled virtual C-arm, having a frame of reference that is relatable to the frame of reference of a surgical tool, such that it can autonomously guide the surgical tool using intraoperative images generated using the virtual C-arm. Such a system, has more versatile functionality and higher accuracy than robotic systems which use registration or navigation or tracking to define the surgical tool for performing the surgical plan.

The systems are based on a twofold combination of at least two robotic arms to enable these novel features to be achieved during surgery. The robotic arms are mounted on a common base, this term being understood to include both having all of the arms mounted on a single base or alternatively having at least some of the arms mounted on separate bases, with the mutual spatial positions of those bases being known to each other. The term "common base" is also thuswise claimed. Because of this feature of a common base, the coordinate system in which each robotic arm operates, can be uniquely related to the coordinate systems of all of the other robotic arms in the system. This feature is important because it enables all of the arms to function co-operatively.

A first pair of arms is provided, in which one arm holds the imaging system source, and the other arm holds the collector or detector element for generating the image itself of the surgical region. The arms are robotically guided, such that their absolute position and orientation in space, and relative to each other, is known at all times. Consequently, they can adopt any source-sensor position desired, according to the robotic control commands issued to them. The reference frame of such an imaging system is known relative to the common base of all of the robotic arms, and hence also to the reference frames of any other robotic arms mounted on the common base. Since the robotic arms are an integral part of the robotic surgical suite, there is no need for a separate C-arm imager, which would take up valuable space in the operating room, and requires a medical technician and alignment time to operate it. The imaging system can be of any suitable type, including an X-ray imager, an ultrasound imager, or any other type of imaging system having separate source and detection elements for mounting on separate robotic arms of the system. However, since the most commonly used such imaging system is the X-ray system, as used on the usual C-arm systems, the disclosure herewith uses the X-ray example for describing the imaging system and its operation, though it must be emphasized that the system and methods are not intended to be limited to X-ray imaging.

The current system differs, however, from previously proposed virtual C-arm systems, this term being used to describe imaging systems in which the X-ray source and the X-ray detection device are mounted on co-related controlled robotic arms, in that a surgical tool is positioned, and its operation optionally also controlled, by a robotic arm whose coordinate system is known to the coordinate system of the X-ray imaging system. One method of achieving this is by using a third robotic arm to carry and position or activate the surgical tool. The third arm may even be an active robotic arm, which can be equipped with a surgical scalpel, a surgical drill, a guide tube, a retractor, or some other surgical tool, and which can then perform a robotically controlled surgical action on the patient. The use of an active robotic arm in this system is advantageous, since the pose of the surgical tool is then known with high accuracy relative to the fluoroscopic imaged data, since the coordinate systems of the third robotic arm carrying the tool is known to the control system of the co-ordinate system of the imaging stage, the co-ordinate systems of all of the arms being co-related to each other. Thus the position of the surgical tool is achieved with the same robotic control as was used in aligning the imaging stage, and can be guided to a position which is known on the fluoroscopic images obtained by the system.

According to a second and generally simpler implementation of such systems, the surgical tool holder is mounted on the same robotic arm as one of the imaging components, preferably the detection plate since it is substantially lighter than the X-ray source, such that the pose of the surgical tool is known relative to the X-ray detection plate with high accuracy. The tool can most advantageously be mounted on a holder which is attached to the same robotic arm as the detection plate, such that the comparative pose of the tool and the detection plate are known and fixed. This provides the optimum accuracy of position between the tool and the other robotically moved imaging elements. Alternatively, the detection plate can be provided with an accurate demountable attachment fixture to its robotic arm, and the tool-holder equipped with a similar demountable attachment fixture, such that the tool can be mounted on the arm instead of the detection plate in much the same way as the tool exchanger in a machine tool operates. In either of these two implementations the surgical tool performs the surgical operation in the same reference frame as that in which the images were acquired. Once the required imaging has been performed using the imaging pair of robotic arms, the detection plate can be demounted and the tool assembly mounted in its place, such that the surgical tool can then perform a surgical action on the patient, with the same advantages as those mentioned in the previous paragraph. Both of these implementations provide improved tool position accuracy than types of registration procedure using preoperative images to define the tool insertion pose, in which the tool position is not directly related to the co-ordinates of the imaging system.

In such an arrangement of using only two robotically controlled arms, a third robotic arm can then also be used to perform another associated surgical action, such as a retraction or holding action in conjunction with the surgical operation procedure being performed by the now "vacated" arm of the imaging pair of arms.

One exemplary procedure by which the system is able to align the tool using only fluoroscopic images obtained intraoperatively using the robotically controlled arms, could be as follows:

(i) Two or more X-ray images are generated by the two imaging robot arms, thereby obtaining a three-dimensional image set.

(ii) The surgical plan is then generated by the surgeon directly on the intraoperative fluoroscope images in real time, and the three dimensional properties of the plan are achieved by generating the plan on two non-coplanar imaging planes, most conveniently, on two perpendicular imaging planes.

(iii) As an additional and optional step, and using the case of a drilling procedure as a non-limiting example, the robot arm carrying the detector may then be controllably moved to be generally perpendicular to the drilling trajectory decided by the surgeon, and a further 2-D image taken for verification, to ensure that the drill trajectory does not encroach on any forbidden areas.

(iv) Finally, the robot arm carrying the detector, which also has a drill guide or a drill connected adjacently to the detector, or which has an interchangeable tool holder to be inserted instead of the detector, is moved automatically to align the drill guide or the drill to point along the drilling trajectory planned.

In the above described procedure, use is made only of the two dimensional fluoroscope images to align the tool or its guide along the correct trajectory, and there is no need for registration at all since there is no preoperative planning—the "planning" is based on direct vision of the subject's anatomy in the fluoroscope images. Although present day registration techniques have good accuracy, the elimination of the need for this step eliminates any potential inaccuracy which may arise with such a registration procedure.

Another advantages of using the imaging robot of the present disclosure is the ability to automatically detect the correct trajectory according to an algorithm that calculates the correct trajectory from images in a machine vision and machine learning mode. In such procedures, the robot takes one or more x-ray images, and, based on this algorithm moves the detector to the expected straight-on view of the region of interest, and takes successive images until it converges to an image approved by the surgeon to apply the surgical act.

According to further implementations of the above described systems, input from preoperative three-dimensional image data, showing either fiducial markers or anatomical details, can also be used in order to register a preoperative surgical plan produced on the preoperative three-dimensional image data, with real time fluoroscopic images obtained from the X-ray fluoroscopic imager mounted on the imaging pair of robotic arms. Such a registration will then enable monitoring the action of the surgical tool and of its accuracy relative to the preoperative plan. This procedure thus enables high resolution preoperative three-dimensional images, such as CT or MRI image sets, to be used as the basis for defining the pose of the tool held in one of the robotic arms. This procedure enables the system to perform a surgical procedure with the advantages both of real-time intraoperative imaging and of high resolution preoperative three-dimensional images. Though less convenient and potentially having somewhat reduced accuracy than the use of the intraoperative surgical planning methods described previously in this disclosure, in which intraoperative imaging is used using combinations of fluoroscope images, this use of planning on the basis of preoperative high resolution images may be advantageous when the region of interest contains features which do not enable the provision of high quality fluoroscope images, such as when there are only soft tissues, or when there is a preponderance of opaque bone structures in the region of interest.

There is thus provided in accordance with an exemplary implementation of the devices described in this disclosure, a system for a robotic surgical system comprising:
(i) a first robotic arm configured to carry an imager source,
(ii) a second robotic arm mounted in a known position relative to the first robotic arm, and configured to carry an imager detection element, the two robotic arms mounted such that when a subject is positioned between the two arms, images of a region of interest of the subject can be generated, and
(iii) a controller configured to co-relate the co-ordinate systems of the robotic arms,
wherein one of the robotic arms is further configured to carry a surgical tool or a surgical tool holder, such that the pose of the surgical tool or tool holder is known relative to the images generated of the subject.

In such a system, the surgical tool or tool holder may be carried on one of the first or second robotic arms in addition to the source or detection element, or it may be carried on one of the first or second robotic arms in place of the source or detection element.

Furthermore, in such a system, the robotic arm configured to carry a surgical tool or a surgical tool holder may be the second robotic arm. This second robotic arm may be adapted to carry simultaneously, both the surgical tool or tool holder, and the detection element in a known spatial relationship.

Additionally, the second robotic arm may comprise an attachment element adapted to be attached either to the surgical tool or tool holder, or to the detection element, the attachment element being such that the spatial relationship between the surgical tool or tool holder, and the detection element is accurately known.

In any of the above described systems, the known relationship between the tool or tool holder, and at least one of the robotic arms may be configured to enable autonomous guidance of the surgical tool to a position on the images obtained by use of the first and second robotic arms, determined by a user.

Furthermore, any of the above described systems may further comprise a third robotic arm whose co-ordinate system is co-related to those of the first and second robotic arms, and which is adapted to hold additional surgical elements.

In all of the above described systems, the imager may be either an X-ray imager or an ultrasound imager.

There is further provided according to other implementations of the robotic surgical systems of the present disclosure, a system comprising at least first, second and third robotic arms, the robotic arms being mutually mounted such that their co-ordinate systems are known relative to each other, at least the first and the second robotic arms being disposed on opposite sides of a support element on which a subject may be positioned, and which are configured to carry respectively an imager source and an imager detection element such that images of a portion of the subject's anatomy can be generated,
wherein the third robotic arm may be configured to carry a surgical tool holder or tool, such that the pose of the surgical tool or tool holder is known relative to images generated by the first and second robotic arms. In such a system, the imager may be either an X-ray imager or an ultrasound imager.

According to yet further implementations, there is provided a method of performing a surgical procedure on a region of a subject, comprising:
(i) generating at least one image including the region of the subject, by means of a source carried on a first robotic arm, and a detector element carried on a second robotic arm, the first and second robotic arms having a commonly related co-ordinate system,
(ii) determining in real time on at least one image, a trajectory necessary for performing the procedure, and
(iii) using a surgical tool carried on one of the first robotic arm or the second robotic arm or a third robotic arm to implement the procedure, after alignment of the robotic arm carrying the tool to ensure the determined trajectory on the at least one image.

In such a method, if the surgical tool is carried on one of the first or second robotic arms, it may be carried either in addition to the imager source or detector element, or may be carried in place of the imager source or detector element. Additionally, if it is carried on the third robotic arm, the trajectory necessary for performing the procedure is assured by virtue of the commonly related coordinate systems of the third robotic arm to those of the first and second robotic arms. In any of these methods, the procedure may be performed using intraoperative alignment of the tool trajectory in at least one image generated using the imaging system having a co-ordinate system common to that of the tool.

There is further provided a method of performing a surgical procedure on a region of a subject, comprising:

(i) generating a preoperative three dimensional set of images including the region of the subject,
(ii) planning preoperatively on the three dimensional set of images, a trajectory for a surgical tool to perform the surgical procedure,
(iii) registering the three dimensional set of images with at least one intraoperative two dimensional image generated by an imager source carried on a first robotic arm, and an imager detector element carried on a second robotic arm, the first and second robotic arms having commonly known co-ordinate systems, wherein the surgical tool may be carried either on the second robotic arm or on a third robotic arm whose coordinate system is co-related to that of the first and second robotic arms, such that manipulation of the robotic arm carrying the tool implements in real time, the preoperatively planned trajectory. In such a method, the surgical tool may be carried on the second robotic arm in addition to the imager detector element, or in place of the imager detector element.

According to yet another exemplary implementation of the present systems, there is provided a robotic surgical system comprising:
at least first, second and third robotic arms, the robotic arms being mutually mounted such that the co-ordinate systems of the robotic arms are known relative to each other,
wherein at least the first and the second robotic arms may be disposed on opposite sides of a support element on which a subject is to be positioned, and are configured to carry respectively an imager source and an imager detection element such that images of a portion of the subject's anatomy can be generated, and
wherein the third robotic arm is adapted to carry a first surgical tool, and
wherein the second robotic arm is further configured to carry a second surgical tool, such that a surgical procedure can be performed using the first and second surgical tools, and
wherein the pose of the first and second surgical tools are known relative to the co-ordinate system of images of the subject generated using the first and the second robotic arms.

Finally, according to yet another implementation of the systems of the present disclosure, there is proposed a robotic surgical system comprising:
at least a first and a second robotic arms, the robotic arms being mounted in mutually known positions such that their co-ordinate systems are known relative to each other, and being disposed on opposite sides of a support element on which a subject is to be positioned, the first robotic arm being configured to carry an imager source and the second robotic arm being configured to carry an imager detection element, such that images defining a portion of the subject's anatomy can be generated,
wherein one of the robotic arms may be further configured to carry a surgical tool or a tool holder, such that the pose of the surgical tool or tool holder is known relative to the images generated of the subject.

BRIEF DESCRIPTION OF THE DRAWINGS

The present invention will be understood and appreciated more fully from the following detailed description, taken in conjunction with the drawings in which.

DETAILED DESCRIPTION

Figure 1:
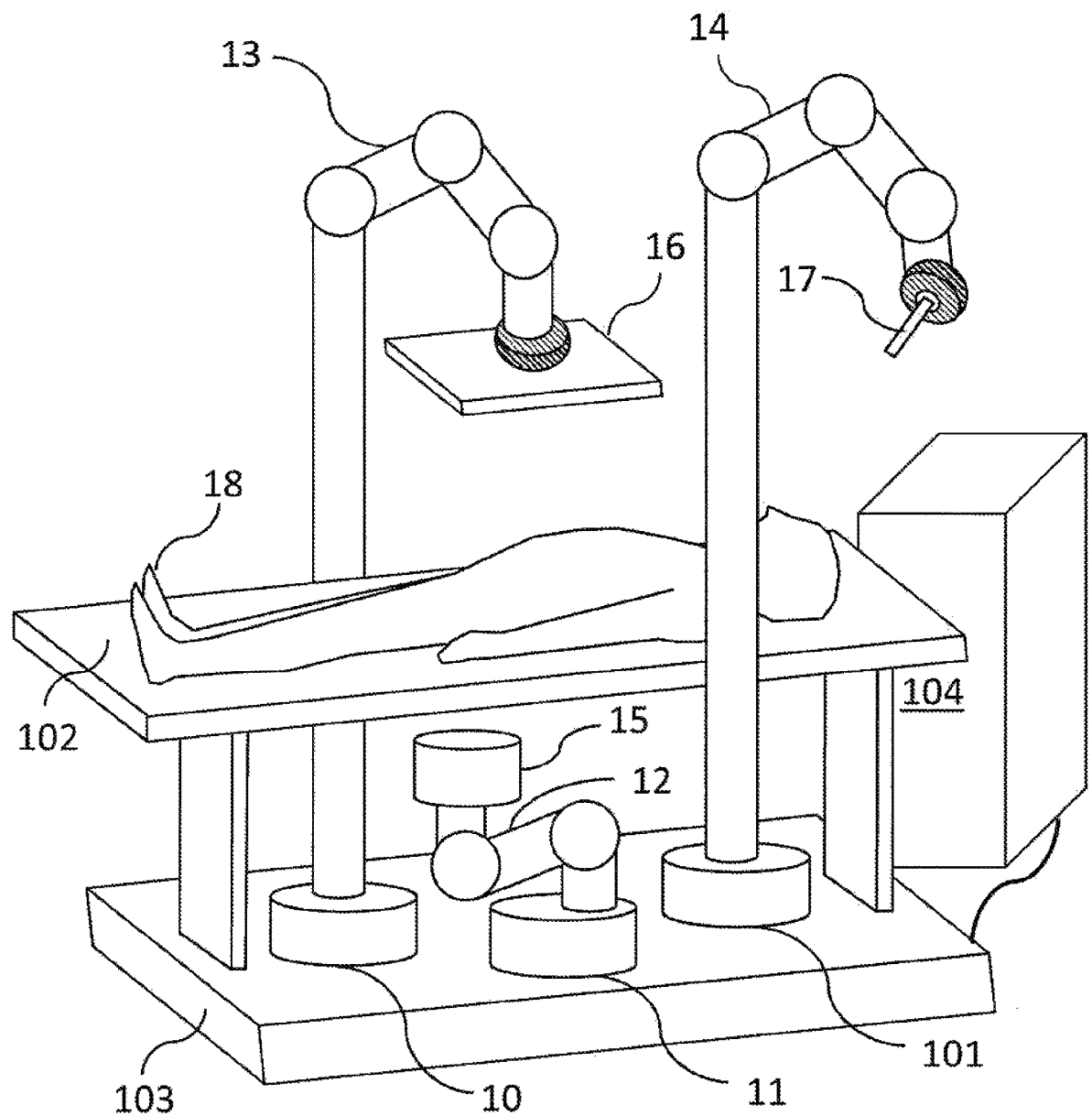
FIG. 1 shows a robotic surgical system as described in the present disclosure, showing three robotically activated, coordinated arms.

Reference is now made to FIG. 1, which illustrates schematically a robotic surgical system as described in the present disclosure, incorporating three robotically activated arms 12, 13, 14. The arms of the system shown in FIG. 1 are mounted on separate bases 10, 11, 101, whose mutual position is known, such that they can be considered as being a single common base 103. Any other base arrangement can also be considered, provided that the positions of the attachments of the robotic arms to the base are known, such that the pose of each of the arms can be co-related to each other. Typically, the arms 13, 14, operating on the top side of the surgical bed 102, may be mounted on an upper console. The arms are controlled by a controller 104, which registers or coordinates the frame of reference of the three arms, and which may be connected to each arm and its control motors and position encoders through the base 104. The patient 18 is shown lying on a bed or operating table 102, though the system could also be used with a standing patient, or a patent in any other desired position, if suitably adapted and aligned. One pair of arms 12, 13, are shown aligned above and below the patient, with one of the arms 12 carrying an X-ray source 15, while the other arm 13, carrying an image detector plate 16. By controlling the joints of these two arms 12, 13, the X-ray source and detector plate can be aligned at any suitable angle relative to the patient's anatomy, to generate a fluoroscopic image of a desired feature of the surgical region. If two or more of such fluoroscopic images are generated, the control system of the surgical robotics suite can provide three-dimensional image data of the surgical site, which can then be used to determine the real time position of the surgical region of interest of the patient in three dimensions. Alternatively, such three dimensional information can be registered and compared with any preoperative three dimensional images on which a surgical plan has been determined, provided some sort of fiducial position feature had been used in the preoperative images.

A third robotic arm 14, can carry a surgical tool 17, or a surgical tool holder, and since the frame of reference of this third robotic arm 14 is known relative to those of the first and second arms 12,13, the position and orientation of the surgical tool is known relative to the co-ordinate system of the fluoroscopic images generated on the imager arranged on the first 12 and second 13 arms. Consequently, the relative position and progress of the surgical tool 17 during the operation can be directly related to the fluoroscopic images of the surgical site of the patient, without the need for further external registration.

According to an alternative mode of operation, once the fluoroscopic image or images have been generated to define the features of the surgical site of the patient, at least one element of the X-ray imaging equipment may be removed from its supporting robotic arm—preferably the detector plate 16 from the robotic arm 13, since that is the lighter element—and that robotic arm 13, is then free to be equipped with a surgical tool or tool holder, whose pose is known relative to the previously generated X-ray images, by virtue of the tool being attached at a known position and angle to the robotic arm 13, whose position is known relative to the X-ray images axis. Alignment and progress of the tool using the robotic control system of the robotic arm 13, can therefore be directly related to the fluoroscopic images previously obtained, without the need for any registration transformation. The third robotic arm 14, since it is no longer required to hold the tool holder or tool, can then be used to perform an additional surgical task, such as retraction or holding of the patient's tissue.

Figure 2:
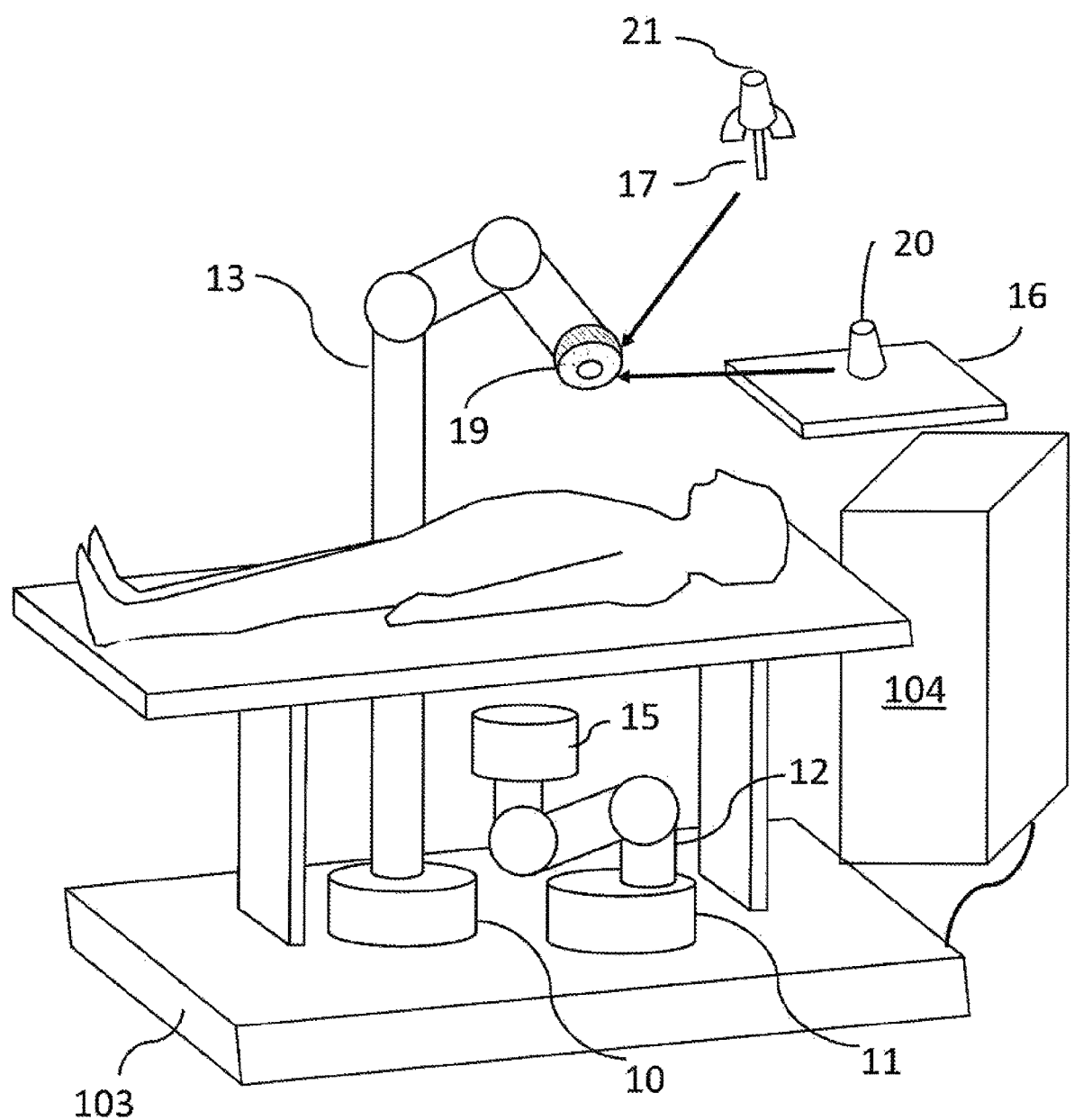
FIG. 2 shows an alternative implementation of the system of FIG. 1, in which only two robotic arms are used.

Reference is now made to FIG. 2, which shows this alternative implementation of the systems of the present disclosure, in which only two robotic arms are used—a first robotic arm 12 carrying an X-ray source 15, while the second robotic arm 13 is equipped with an adapter mount 19, which can be connected either to the X-ray sensor plate 16 by means of the matching adapter 20, or to a tool or tool holder 17, by means of the adaptor 21, the adaptors being such that the relative position of the X-ray sensor plate and the tool or tool holder are known to a high level of accuracy. In this implementation, the robotic control system 104 controls the motion of both robotic arms 12, 13. Each robotic arm is adapted to hold at least one surgical tool or other item for use during a surgical operation. The robotic arm 13 has a base 10 that could equally well be attached to the ceiling or another immobile support element in the room, or upon a control cabinet. The second robotic arm 12 is shown also attached to an immovable support element 11. The controller 104 can manipulate the movements of each robotic arm such that the position of the surgical tool or other items held and carried by each arm are known with precision relative to each other.

Figure 3:
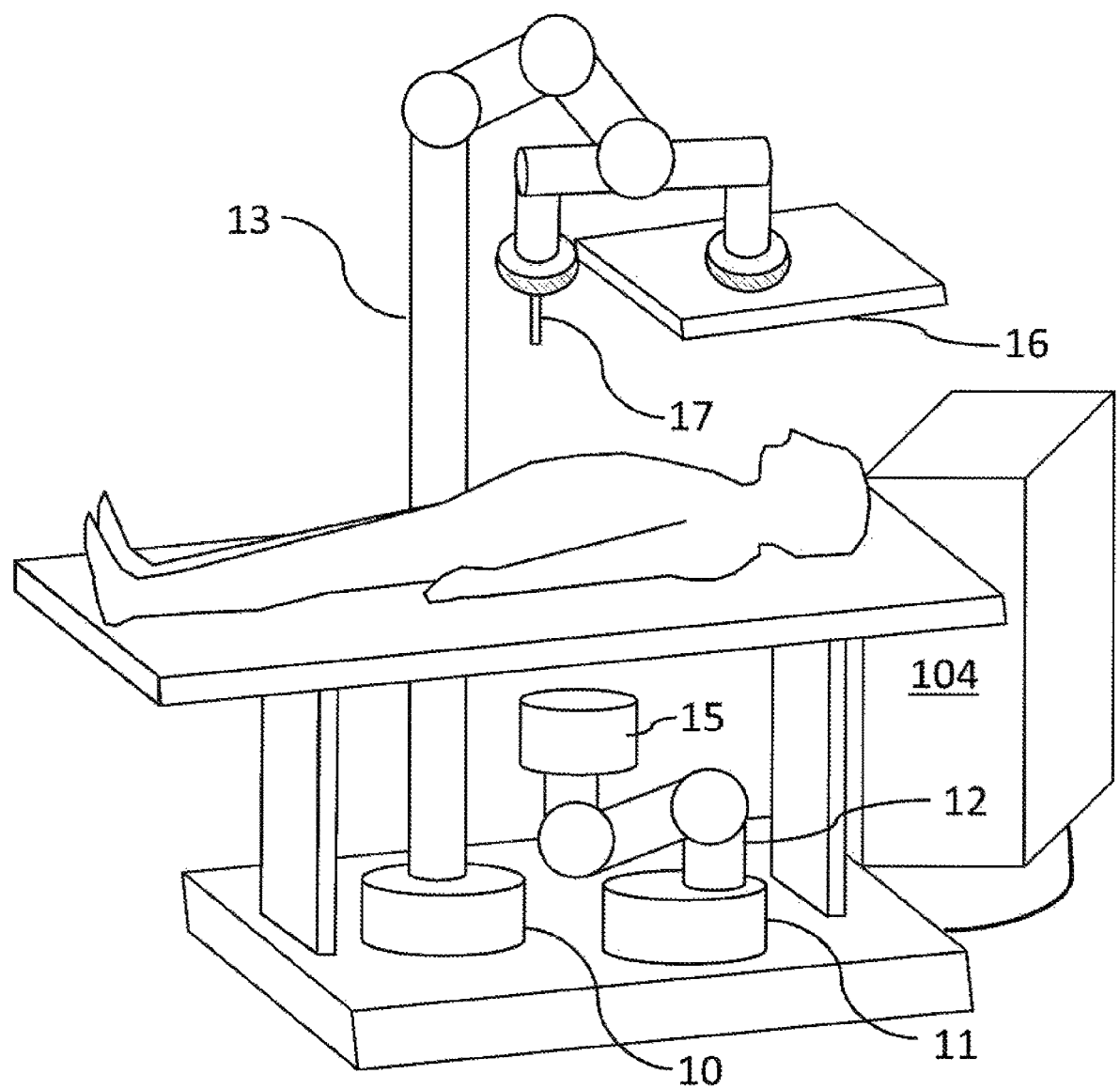
FIG. 3 shows an alternative implementation to that of FIG. 2, in which the tool or tool holder and the X-ray detector plate are both held together in the same robotic arm, their mutual position being known to the robotic control system by virtue of the known mechanical arrangement connecting them.

Reference is now made to FIG. 3, which shows an alternative implementation to that of FIG. 2, in which the tool or tool holder 17 and the X-ray detector plate 16 are both held in the robotic arm 13, their mutual position being known to the robotic control system by virtue of the known mechanical arrangement connecting them. Therefore, the position of the tool 17 relative to the imaged view of the patient generated on the detection plate 16, is accurately known. This implementation avoids the need to exchange the detector plate with the tool holder.

In any of the above described implementations, image processing of the X-ray images can be used to define the position of the patient, or anatomical features of the patient to be operated on, and the known relationship between the imaging frame of reference and the tool frame of reference, enables accurate positioning of the tool relative to the patient or the anatomical feature of the patient to be operated on. Such a system can be configured to autonomously guide a surgical tool to a position which is known on the X-ray images obtained by the system itself, without the need for any other alignment, since the frame of reference used for generating the images can be spatially and angularly related to the frame of reference in which the tool is mounted.

Figure 4:
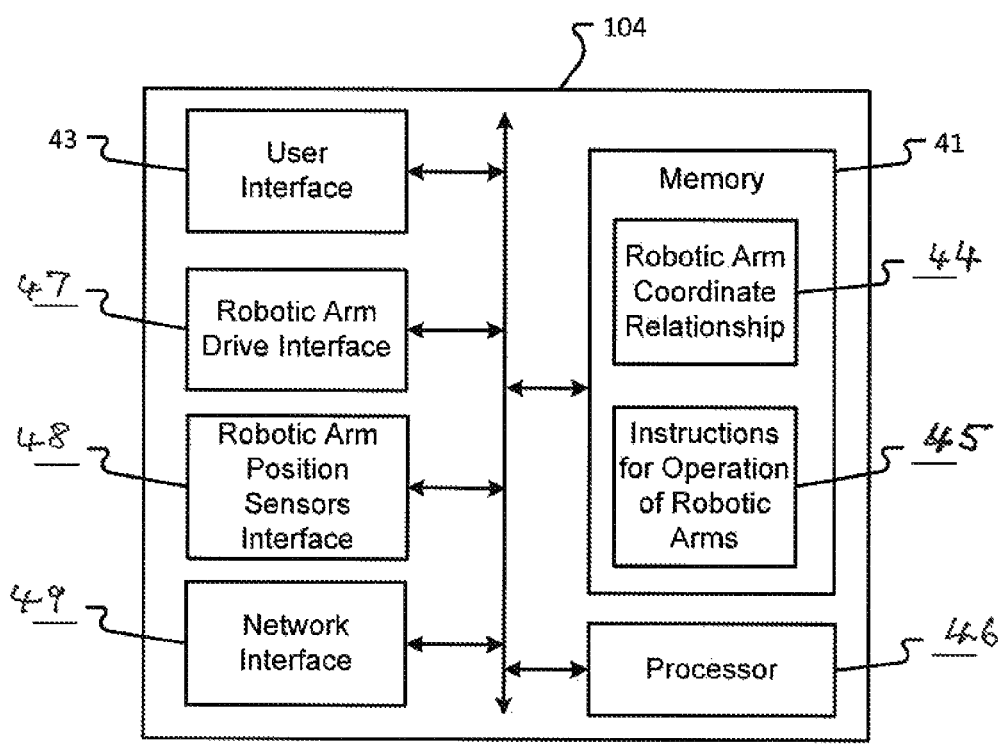
FIG. 4 shows one example of the structure of the system controller with its memory unit, showing how the relationship between a robotic imaging arm and the tool holding arm is used to direct the tool to perform its required function.

Reference is now made to FIG. 4, which illustrates schematically one possible structure of the control system 104, enabling the functioning of the system. The controller and system functionality uses a memory unit 41, which contains the Robotic Arm Coordinate Relationship 44, and the instructions for the operation of the Robotic Arms 45.

The processor 46 controls the entire controller operation, including input-output and calculations. The input output units include a user interface 43, a robotic arm drive interface 47, a robotic arm position sensors interface 48 and a network interface 49.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A robotic surgical system comprising:
   a first robotic arm configured to carry an imager source; and
   a second robotic arm mounted in a known position relative to the first robotic arm, and configured to carry an imager detection element, the first robotic arm and the second robotic arm mounted such that when a subject is positioned between the first robotic arm and the second robotic arm, images of a region of interest of the subject can be generated,
   wherein the known position of the second robotic arm relative to the first robotic arm is based on a known mechanical arrangement connecting the first robotic arm and the second robotic arm,
   wherein the known mechanical arrangement is defined by the first robotic arm connected to a common base with the second robotic arm, and
   wherein the second robotic arm is further configured to carry a surgical tool or a surgical tool holder and the imager detection element in a fixed spatial relationship, such that a pose of the surgical tool or the surgical tool holder is known relative to the images generated of the subject.

2. The robotic surgical system according to claim 1, wherein the second robotic arm comprises an attachment element adapted to be attached either to the surgical tool or the surgical tool holder, the attachment element being such that the fixed spatial relationship between the surgical tool or tool holder and the imager detection element is accurately known.

3. The robotic surgical system according to claim 1, wherein the pose of the surgical tool or the surgical tool holder enables autonomous guidance of the surgical tool to a position on the images generated of the subject, determined by a user.

4. The robotic surgical system according to claim 1, further comprising a third robotic arm whose co-ordinate system is co-related to those of the first and second robotic arms, and which is adapted to hold additional surgical elements.

5. The robotic surgical system according to claim 1, wherein the imager source is either an X-ray imager or an ultrasound imager.

6. The robotic surgical system according to claim 1, further comprising:
   a controller configured to co-relate co-ordinate systems of the first and second robotic arms.

7. The robotic surgical system according to claim 1, wherein the surgical tool comprises at least one of a surgical scalpel, a surgical drill, a guide tube, and a retractor.

8. The robotic surgical system according to claim 1, wherein the images of the region of interest correspond to fluoroscopic images.

9. The robotic surgical system according to claim 8, wherein positioning of the surgical tool is achieved with a same robotic control as was used in aligning an imaging stage, and wherein the surgical tool can be guided to a position which is known on the fluoroscopic images obtained by the system.

10. A robotic surgical system comprising:
at least a first robotic arm and a second robotic arm, the first robotic arm and the second robotic arm being mutually mounted such that their co-ordinate systems are known relative to each other, the first robotic arm being disposed on a first side of a support element and the second robotic arm being disposed on a second side of the support element on which a subject is to be positioned, and being configured to carry respectively an imager source and an imager detection element such that images of a portion of the subject's anatomy can be generated,
wherein the second robotic arm is mounted in a known position relative to the first robotic arm,
wherein the known position of the second robotic arm relative to the first robotic arm is based on a known mechanical arrangement connecting the first robotic arm and the second robotic arm,
wherein the known mechanical arrangement is defined by the first robotic arm being connected to a common base with the second robotic arm, and
wherein the second robotic arm is configured to carry a surgical tool or a surgical tool holder and the imager detection element in a fixed spatial relationship, such that a pose of the surgical tool or the surgical tool holder is known relative to images generated of the subject.

11. The robotic surgical system according to claim 10, wherein the imager source is either an X-ray imager or an ultrasound imager.

12. A method of performing a surgical procedure on a region of a subject, comprising:
generating at least one image including the region of the subject, by means of a source carried on a first robotic arm, and a detector element carried on a second robotic arm, the first and second robotic arms having a commonly related co-ordinate system, the second robotic arm mounted in a known position relative to the first robotic arm,
wherein the known position of the second robotic arm relative to the first robotic arm is based on a known mechanical arrangement connecting the first robotic arm and the second robotic arm, and wherein the known mechanical arrangement is defined by the first robotic arm being on a common base with the second robotic arm;
determining, on the at least one image, a trajectory necessary for performing the surgical procedure; and
using a surgical tool carried on the second robotic arm to implement the surgical procedure, wherein the second robotic arm is configured to carry the surgical tool and the detector element in a fixed spatial relationship, such that a pose of the surgical tool is known relative to the at least one image generated of the subject.

13. The method according to claim 12, wherein the surgical procedure is performed using intraoperative alignment of a tool trajectory in the at least one image generated having a co-ordinate system common to that of the surgical tool.

14. The method according to claim 12, wherein determining the trajectory includes determining the trajectory in real-time.

15. The method according to claim 12, wherein the at least one image is a three-dimensional set of images.

16. The method according to claim 15, further comprising:
registering the three-dimensional set of images with at least one intraoperative two-dimensional image generated by the source and the detector element.

17. The method according to claim 12, wherein the at least one image is generated preoperatively, and wherein determining the trajectory includes determining the trajectory preoperatively.

18. The method according to claim 12, wherein the surgical tool comprises at least one of a surgical scalpel, a surgical drill, a guide tube, and a retractor.

19. The method according to claim 12, wherein the at least one image including the region of the subject correspond to at least one fluoroscopic image.

20. The method according to claim 19, wherein positioning of the surgical tool is achieved with a same robotic control as was used in aligning an imaging stage, and wherein the surgical tool can be guided to a position which is known on the at least one fluoroscopic image generated.

* * * * *